United States Patent [19]

Rhodes et al.

[11] 4,222,923

[45] Sep. 16, 1980

[54] ADHESIVE COMPOSITION AND METHOD OF USE

[76] Inventors: John Rhodes, 25 Nant Fawr Rd. Cyncoed, Cardiff, Wales; William Douglas, 2321 Stone Dr., Ann Arbor, Mich. 48105

[21] Appl. No.: 897,389

[22] Filed: Apr. 18, 1978

Related U.S. Application Data

[63] Continuation-in-part of Ser. No. 882,752, Mar. 2, 1978, abandoned.

[30] Foreign Application Priority Data

Mar. 2, 1978 [GB] United Kingdom ............... 9326/78

[51] Int. Cl.$^2$ ..................... C08K 5/10; C08L 27/24
[52] U.S. Cl. ........................... 260/31.8 DR; 128/275; 128/283; 260/31.8 M; 260/31.8 G; 260/32.6 A; 260/32.6 PQ; 260/32.8 A; 260/33.2 R; 260/33.4 R; 260/33.8 UA; 260/42.47; 260/42.54; 525/215

[58] Field of Search ............... 260/31.8 DR, 31.8 M, 260/31.8 G, 32.6 A, 32.6 PQ, 42.47, 42.54, 890, 32.8 A, 33.2 R, 33.4 R, 33.8 UA; 525/215

[56] References Cited

U.S. PATENT DOCUMENTS

| 2,332,263 | 10/1943 | Sarbach ...................... 260/31.8 DR |
| 2,734,884 | 2/1956 | Smith, Jr. et al. ........... 260/31.8 DR |
| 2,947,710 | 8/1960 | Frantz ................................. 260/890 |
| 3,092,250 | 6/1963 | Knutson et al. ..................... 260/890 |

*Primary Examiner*—J. Ziegler
*Attorney, Agent, or Firm*—Hammond & Littell, Weissenberger & Muserlian

[57] ABSTRACT

An adhesive composition consisting essentially of a poly (lower alkyl) methacrylate, a liquid plasticizer, an inert particulate filler, and a chlorinated rubber; and a method of using the same to secure the pouch of an ileostomy, ureterostomy, colostomy or the like appliance to the skin.

21 Claims, 1 Drawing Figure

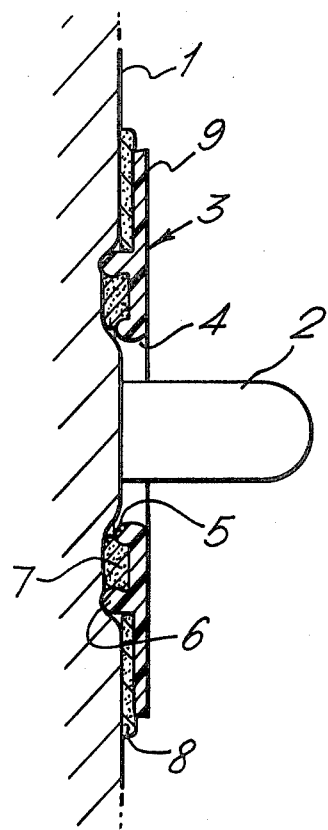

ADHESIVE COMPOSITION AND METHOD OF USE

This is a continuation-in-part of copending application Ser. No. 882,752, filed Mar. 2, 1978, now abandoned.

This invention relates to medical appliances and materials suitable therefor. More particularly, it relates to an adhesive composition which, inter alia, is useful for adhering medical appliances to an animal body.

BACKGROUND OF THE INVENTION

It is often necessary to make an adhesive bond to an animal body, usually a human body, in order to attach a medical appliance or device. Although many adhesive compositions are known, very few of these are suitable for application to human skin. The requirements for such as adhesive are stringent; it must bond strongly to human skin, yet be peelable without damage to the skin's surface. Furthermore, it must cause no inflammation, even on prolonged contact, and should have a minimal tendency to provoke allergy. It must be free of any substances which may be carcinogenic. The requirement to be non-allergenic is particularly difficult to meet, and most adhesives currently available are prone to cause allergies in a significant proportion of patients. When the patient has a tendency to allergy, it may be necessary to test a number of adhesives before one is found which is compatible. This is time-consuming for the doctor, and in the meantime the patient is caused distress by allergic reactions.

DESCRIPTION OF THE INVENTION

This invention provides an adhesive composition consisting of a gelled mixture of:
(1) a poly (lower alkyl) methacrylate,
(2) a physiologically compatible liquid plasticizer,
(3) an inert particulate filler, and
(4) a chlorinated rubber.

The lower alkyl groups in the poly (lower alkyl) methacrylate contain 1-4 carbon atoms; a preferred polymer is polyethyl methacrylate. The poly (lower alkyl) methacrylate is a brittle solid, preferably having a molecular weight in the range 50,000–1,000,000, more preferably in the range 100,000–500,000, for example about 200,000.

The plasticizer component is a liquid which is physiologically compatible and serves to plasticize the poly (lower alkyl) methacrylate. A preferred group of plasticizers are ester plasticizers, particularly esters of dicarboxylic acid. Although diesters of aliphatic dicarboxylic acids may be found with suitable properties, we prefer diesters of aromatic dicarboxylic acids, especially phthalate diesters. The alcoholic components of such phthalate diesters may, for example, be selected from alkanols, alkoxycarbonyl-substituted alkanols and aralkanols. The alkanols may, for example, have 1-8 carbon atoms and be optionally substituted by a lower alkoxycarbonyl reside. A plasticizer which is particularly satisfactory in all respects is butyl phthalyl butyl glycollate. This compound is currently available from Monsanto as "Santicizer B16". Other phthalate diesters which can be used include butyl benzyl phthalate, also available from Monsanto as "Santicizer 160".

Another group of plasticizers of interest for use in this invention are N-substituted arylsulfonamides. The aryl residue may, for example, be phenyl optionally substituted by lower alkyl, such as tolyl. The N-substituent is preferably lower alkyl. An example of such a plasticizer is N-ethyl-o,p-toluenesulfonamide, available from Monsanto as "Santicizer 8".

The precise chemical nature of the plasticizer is not critical to the invention, but it must be physically compatible with the other components of the composition and it must also be physiologically compatible. So far as possible, it should be non-allergenic.

The inert particulate filler serves to stabilize the composition in the form of a cohesive gel. The filler also reduces the tackiness of the composition, and the proportion and nature of filler should be selected to produce the degree of tackiness required. Without any filler, the tack is very aggressive and the adhesion to human skin is difficult to break without damage to the skin. The preferred filler is silica. The filler is preferably of colloidal particle size. Other fillers include finely divided calcium carbonate and diatomaceous earth and silicates such as powdered glass, especially barium glass, lithium aluminium silicates or talcum.

The chlorinated rubber improves the tackiness and cohesion of the composition. Preferred chlorinated rubbers are highly chlorinated hydrocarbons, such as the highly chlorinated polyisoprene available from Imperial Chemical Industries as Alloprene 20.

The proportions of the various components in the composition, per 100 ml of a plasticizer, may for example be as follows: poly (lower alkyl) methacrylate 16–84 gm, preferably 20–45 gm; filler 6–16 gm; preferably 8–12 gm; and chlorinated rubber 16–67 gm, preferably 20–40 gm. The relative proportions of the components should be adjusted within these ranges to give products with the desired properties. Optimum relative proportions for any particular desired combination of properties can be determined by simple experiments.

The composition may be prepared by dispersing the poly (lower alkyl) methacrylate, in powder form, in the plasticizer and causing or allowing the powder to dissolve in the plasticizer to form a gel. The filler and the chlorinated rubber may be added at any stage, preferably while the viscosity is still low enough to enable thorough mixing. In a preferred mixing procedure, the filler is admixed with the plasticizer, the poly (lower alkyl) methacrylate is then added, and finally the chlorinated rubber is added.

The mixture is initially a stiff paste which converts to a homogeneous gel as the plasticizer dissolves the poly (lower alkyl) methacrylate. This conversion proceeds slowly at room temperature and is accelerated by heating, for instance to 40–80° C. Higher or lower temperatures can be used where convenient. At 60° C., the conversion may typically be completed in about 4 to 5 hours. The conversion time depends largely on the state of subdivision of the poly (lower alkyl) methacrylate. Preferably, this material is in the form of powder in the range 50–400 mesh (British Standard Sieve), preferably below 200 mesh.

After conversion, the composition is a translucent flexible gel of rubbery consistency and tacky to the touch. It has good adhesion to human skin. The material is stable; that is to say, it remains cohesive, does not flow at higher filler concentrations and retains its tackiness and adhesivity over long periods of storage and use.

It is often convenient to gel the composition in situ on a surface to be rendered adhesive. Alternatively the composition may be spread, prior to conversion, on a surface having a release coating and gelled in the form of a layer which can subsequently be laminated onto the article to be rendered adhesive. Another way of applying the composition is by forming a dispersion of the composition in an organic solvent which dissolves all components of the composition except the filler, for instance a chlorinated hydrocarbon such as chloroform or methylene dichloride, applying the dispersion to an article to be rendered adhesive, and evaporating the solvent. Other suitable solvents include lower aliphatic ketones such as acetone; aliphatic ethers such as diethyl ether; and lower alkanols such as ethanol. Other it will be preferred to avoid the use of a solvent, because some patients exhibit allergic reactions to common organic solvents. Thus it may be preferable to roll the composition in paste form into a thin layer between surfaces having a release coating, and apply the composition to the article to be rendered adhesive, either before or after conversion of the mixture to a gel.

The composition has a wide variety of applications as an adhesive, particularly but not exclusively for application to human skin, for example as the adhesive coating of surgical tape and other medical and surgical dressings, coverings and appliances. Such surgical tape or dressing will comprise a flexible substrate bearing the adhesive of the invention on one face thereof. The substrate may be of fabric or a plastic film, especially a microporous plastic film. When a medicated dressing is required, the medicament may be incorporated in the adhesive. Examples of such medicaments include antibiotics, antiseptics, coal tar derivatives (which are of value in certain dermatological conditions) and anitinflammatory compounds, such as steroids. Such dressings may be used for covering wounds or other damaged areas of skin, for instance leg ulcers such as varicose ulcers. For such applications the adhesive has the merit of not adhering in the presence of water. Thus if a dressing is used to cover a damaged and weeping area of skin, it will not adhere to the damaged area but will only adhere to undamaged skin around the periphery.

A particularly advantageous use for the adhesive of the invention is for securing the pouch of an ostomy appliance to the skin around the stoma of a patient. After an ostomy operation, such as an ileostomy, colostomy or ureterostomy, the patient is left with a stoma through which waste material is discharged. The discharge is collected in a pouch, which is periodically replaced. It has been a matter of considerable difficulty to secure the pouch to the patient in a comfortable but leakproof manner.

Thus another aspect of our invention provides an adhesive element for securing the pouch of an ostomy appliance to the skin around the stoma of a patient, said adhesive element comprising a flexible pad having an aperture through which said stoma can pass, a face of said pad bearing an adhesive according to the present invention. The other face may be integral with a wall of the pouch, or the pouch may be attached thereto by any suitable mechanical means, such as by an adhesive.

The pad, which will generally be in the form of a disc having a central aperture, is preferably made of a plastic material. Suitable plastic materials include plasticized acrylic polymers and plasticized vinyl polymers, such as plasticized PVC. Since portions of the pad may come into contact with the patient, it is advisable that the pad should be made of a material which is not liable to provoke any adverse reaction by contact with the human body. In particular, the material should preferably be non-allergenic. Suitable plastic materials may be selected from those used in the dental field. Any accelerator(such as a tertiary amine, peroxide or quinone) used to cure the composition forming the pad should be selected with particular care from this point of view. It may be preferable to cure the composition by exposure to actinic radiation (UV or visible light).

It is preferably for the portion of the pad surrounding the aperture to be relatively stiff while the peripheral portion is more flexible. These conditions may be secured by increasing the thickness of the pad over a central area, and/or by including one or more stiffening webs surrounding the aperture. However the pad as a whole should be sufficiently flexible to avoid discomfort to the patient and to conform closely to the curvature of the abdominal wall.

In a particularly preferred embodiment, the aperture in the pad, on the face to be adhered to the patient, is surrounded by a layer of hydrophilic gum which swells on contact with water. This is preferably contained in a moat between two upstanding webs formed on the pad. The hydrophilic gum which we prefer is karaya gum. In the presence of fluid seeping from the stoma, karaya gum will take up water and swell. The swollen gum provides a good seal to the abdominal wall, and will effectively prevent further fluid from leaking out peripherally. This mechanism protects the adhesive of the invention from moisture.

Instead of karaya gum, other natural or synthetic swellable hydrophilic gums can be used, such as agar, alginates or a suitable grade of polyvinyl alcohol.

The other face of the pad may be formed integrally with the ostomy pouch, or the pouch may be attached by any appropriate mechanical means such as clips or, more preferably, by an adhesive. This face of the pad does not come in contact with the skin, and any suitable adhesive can be used. It is not necessary for this adhesive to be physiologically compatible, although the adhesive of the present invention may often be quite suitable for this purpose as well.

The adhesive of the present invention, in the form of a cohesive sheet, may extend beyond the periphery of the pad, and the exposed face of the adhesive sheet may assist in securing the pouch to the pad. If not used for this purpose, it is preferably to render this exposed face, and the edges of the adhesive sheet, non-tacky to avoid adhesion to clothing and the like.

According to a preferred embodiment, the pouch or bag for collection the discharge from the stoma may be replaced without removing the pad from the patient. This avoids having to tear the whole device from the patient each day. This embodiment is particularly applicable to colostomy appliances. In this embodiment the pouch is preferably secured to the pad by a contact adhesive.

The device described above is particularly useful for ostomy patients but may also be of value for collecting a fistular discharge. If desired, the pad may include means for attachment to a belt, for instance in the form of apertures or projections on opposite edges of the pad (or at opposite ends of a diameter when the pad is circular) for attachment to corresponding fixing means on the end of a belt.

An embodiment of the invention will now be described by way of example with reference to the accompanying drawing, which illustrates an adhesive element according to the invention in cross-section.

Referring to the drawing, the abdominal wall 1 of a patient has been surgically provided with a stoma 2. The adhesive element according to the present invention comprises a disc 3 of plastic material having a central aperture 4. The aperture 4 is surrounded by two concentric webs 5 and 6 forming a moat in which is situated a ring of karaya gum 7. The outer portion of the disc is adhered to the abdominal wall by a sheet of adhesive 8 having the composition given below. The outer face 9 of the disc is available for adhesion of the pouch or bag appropriate to the discharge be to collected.

The composition of the adhesive is as follows: "parts" have the relation of ml to gm for liquids and solids, respectively:

Butyl phthalyl butyl glyollate: 6 parts
Polyethyl methacrylate: 2 parts
Alloprene 20: 2 parts
Colloidal silica: 0.65 parts The butyl phthalyl butyl glycollate is currently available from Monsanto as Santicizer B16. Otherwise it can be made by standard esterification procedures.

Polyethyl methacrylate was in the form of a powder below 240 mesh (British Standard Sieve) and had a mean molecular weight of about 200,000. It was obtained from ADI Plastics Limited, Marton, Blackpool, England.

The Alloprene 20 is a chlorinated polyisoprene, available from Imperial Chemical Industries, (Alloprene Section), Runcorn, Cheshire, England.

The silica was of pharmaceutical grade having a low iron content.

The silica was first mixed with the butyl phthalyl butyl glycollate, and the polyethyl methacrylate and Alloprene were added in turn. A very viscous paste resulted, which was mixed mechanically. The paste was then rolled out between two sheets of silicon-coated paper to a thickness of approximately 1.5 mm and allowed to convert for 6 hours in an oven at 60° C.

After cooling, the adhesive was in the form of a cohesive, extremely tacky sheet which could be cut to the desired size and shape. This adhesive is highly compatible with the human body. Indeed, we have never yet observed any adverse reaction to it, even in patients who are allergic to many conventional medical adhesives. Although we cannot say that this material will never cause allergy, it appears to be superior in this respect to most known adhesives. The adhesive projects some way beyond the disc 3 in order to assist in keeping the device in good contact with the abdominal wall.

Another adhesive composition is as follows:
Butyl benzyl phthalate: 6 ml
Polyethyl methacrylate: 2 gm
Alloprene 20: 2 gm
Colloidal silica: 0.5 gm The polyethyl methacrylate was the same as used in the first adhesive. The mixing and conversion procedure was as described.

The disc 3 was composed of an acrylic copolymer which was made as follows: 16 parts of the polyethyl methacrylate described above were mixed with 10 parts of a liquid mixture having the composition 2% N,N-dimethyl-p-toluidine; 30% ethylene glycol dimethacrylate (available from Rohm & Haas); and 68% of butyl phthalyl butyl glyollate.

The resulting fluid slurry was immediately poured into a mold and cured for 15 minutes at 60° C. to form a flexible, rubbery disc. The accelerator (N,N-dimethyl-p-toliudine) may be replaced by other suitable tertiary amines, but it is preferable to select this material with care to avoid allergy problems.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. An adhesive composition consisting essentially of a gelled mixture of:
   (1) a poly (lower alkyl) methacrylate,
   (2) a physiologically compatible liquid plasticizer,
   (3) an inert particulate filler, and
   (4) a chlorinated rubber.

2. An adhesive composition according to claim 1, wherein said poly (lower alkyl) methacrylate is polyethyl methacrylate.

3. An adhesive composition according to claim 2, where said poly (lower alkyl) methacrylate has a molecular weight in the range 50,000 to 1,000,000.

4. An adhesive composition according to claim 3, where said molecular weight is in the range 100,000 to 500,000.

5. An adhesive composition according to 1, where said plasticizer is a phthalate diester.

6. An adhesive composition according to claim 5, where the alcoholic components of said phthalate diester are selected from alkanols of 1-8 carbon atoms optionally substituted by an alkoxycarbonyl reside, and aralkanols.

7. An adhesive composition according to claim 5, where said plasticizer is butyl phthalyl butyl glycollate.

8. An adhesive composition according to claim 5, where said plasticizer is butyl benzyl phthalate.

9. An adhesive composition according to claim 1, where said plasticizer is an N-(lower alkyl-substituted) arylsulfonamide.

10. An adhesive composition according to claim 9, where said plasticizer is N-ethyl-o,p-toluenesulfonamide.

11. An adhesive composition according to claim 1, where said inert particulate filler is colloidal silica.

12. An adhesive composition according to claim 1, where said chlorinated rubber is a highly chlorinated polyisoprene.

13. An adhesive composition according to claim 1, comprising, per 100 ml of plasticizer, 16-84 gm of poly (lower alkyl) methacrylate; 6-16 gm of said filler; and 16-67 gm of chlorinated rubber.

14. An adhesive composition according to claim 13 comprising, per 100 ml of plasticizer, 20-45 gm of poly (lower alkyl) methacrylate; 8-12 gm of said filler; and 20-40 gm of chlorinated rubber.

15. An adhesive composition according to claim 1, comprising polyethyl methacrylate; butyl phthalyl butyl glycollate as the plasticizer; colloidal silica as the filler; and a chlorinated polyisoprene.

16. An adhesive composition according to claim 1 consisting essentially of a gelled mixture of:
   (1) a physiologically compatible plasticizer comprising a diester of an aromatic dicarboxylic acid or an N-substituted arylsulfonamide;
   (2) from 16 to 84 gm, per 100 ml of plasticizer, of a poly (lower alkyl) methacrylate having a molecular weight in the range of from 50,000 to 1,000,000;

(3) from 6 to 16 gm, per 100 ml of plasticizer, of an inert particulate filler selected from the group consisting of colloidal silica, finely divided calcium carbonate, diatomaceous earth, powdered barium glass, lithium aliminum silicates, and talcum; and
(4) from 16 to 67 gm, per 100 ml of plasticizer, of highly chlorinated polyisoprene.

17. A dispersion of the composition of claim 1 in an organic solvent which dissolves all components of said composition except the filler.

18. The method of making the adhesive composition of claim 1, which comprises mixing the components of said composition and allowing the resultant paste to convert to a homogeneous gelled composition at an elevated temperature.

19. The method according to claim 18, where said elevated temperature is in the range 40–80° C.

20. The method according to claim 18, wherein said poly (lower alkyl) methacrylate has a particle size in the range 50–400 mesh (British Standard Sieve).

21. The method according to claim 18, where said paste is allowed to convert to a homogeneous composition in situ on a surface to be rendered adhesive.

* * * * *